United States Patent [19]
Eom et al.

[11] Patent Number: 6,101,342
[45] Date of Patent: Aug. 8, 2000

[54] APPARATUS AND METHOD FOR MEASURING DEVELOPER CONTAMINATION OF PRINTER

[75] Inventors: Yoon-seop Eom, Suwon; Won-hyung Lee, Seoul; Yong-baek Yoo, Suwon, all of Rep. of Korea

[73] Assignee: Samsung Electronics Co., Ltd., Kyungki-Do, Rep. of Korea

[21] Appl. No.: 09/427,725

[22] Filed: Oct. 27, 1999

[30] Foreign Application Priority Data

Oct. 27, 1998 [KR] Rep. of Korea ...................... 98-44997

[51] Int. Cl.[7] .......................... G03G 13/10; G03G 15/10
[52] U.S. Cl. ................................ 399/29; 399/64; 399/81; 430/117
[58] Field of Search .................................. 399/29, 27, 28, 399/30, 57, 58, 59, 62, 64, 237, 238, 81; 430/117; 222/DIG. 1

[56] References Cited

U.S. PATENT DOCUMENTS 5,722,017  2/1998  Caruthers et al. ...................... 399/238

OTHER PUBLICATIONS

Abstract of Japanese Publication JP-A-60192968, Published Oct. 1, 1985.

*Primary Examiner*—Richard Moses
*Attorney, Agent, or Firm*—Sughrue, Mion, Zinn, Macpeak & Seas, PLLC

[57] ABSTRACT

A developer contamination measuring apparatus of a printer includes a first pipe portion having a first gap and a second pipe portion having a second gap, a light emitting unit radiating light to the first pipe portion and the second pipe portion, a light detecting unit detecting light reflected or transmitted from the first pipe portion and the second pipe portion to output first and second light receiving signals, respectively, and a developer contamination measuring unit controlling the light emitting unit, and calculating the degree of a contamination due to mixing of other developing materials with the developer from the first and the second light receiving signals. Thus, the degree of contamination of a developer mixed with other developing materials can be precisely calculated, and the developer can be replaced, when the calculated amount of contamination exceeds a predetermined allowable contamination level, to thereby prevent deterioration of print quality.

14 Claims, 7 Drawing Sheets

APPARATUS AND METHOD FOR MEASURING DEVELOPER CONTAMINATION OF PRINTER

BACKGROUND OF THE INVENTION

1. Field of the Invention

The present invention relates to an apparatus and a method for measuring contamination of a developer of a printer, and more particularly, to an apparatus and a method for measuring the concentration and contamination of a developer of a printer using data obtained from the developer under various conditions. This application is based on Korean Patent Application 98-44997, which is incorporated by reference herein for all purposes.

2. Description of the Related Art

Figure 1:
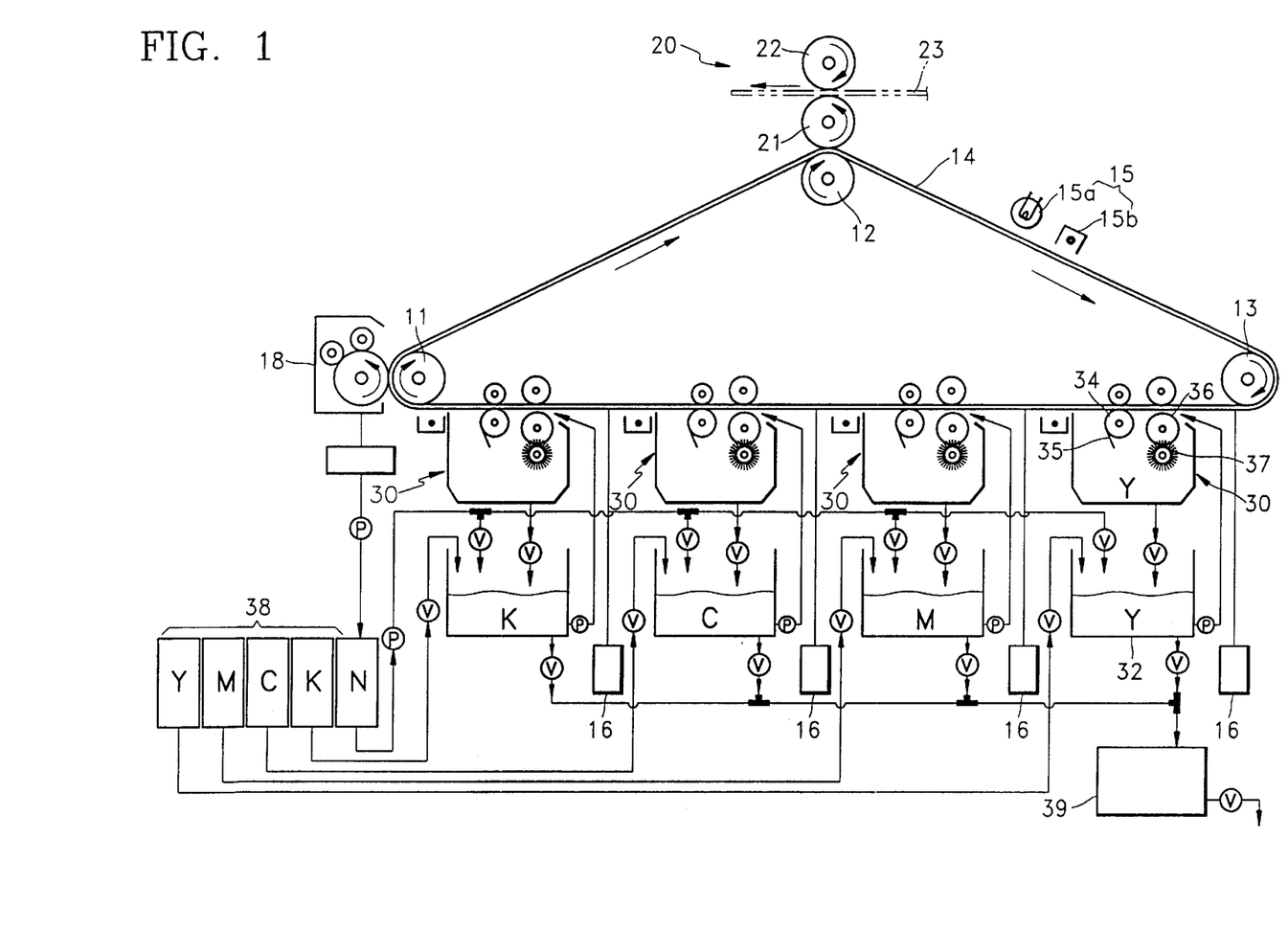
FIG. 1 shows a typical liquid type color printer.

FIG. 1 is a schematic view of a typical liquid type color printer. Referring to FIG. 1, a printer using a developer includes a reset apparatus 15, light scanning units 16, developing units 30, a drier 18, and a transfer apparatus 20, adjacent to the circulation path of a photosensitive belt 14 around a plurality of rollers 11, 12 and 13.

The reset apparatus 15 includes an exposure apparatus 15a radiating beams to the photosensitive belt 14 to remove an electrostatic latent image, and an electrostatic charge unit 15b for charging the photosensitive belt 14 to a predetermined electric potential. Reference numeral 39 denotes a waste tank for collecting waste developer.

The four light scanning units 16 scan information of yellow Y, magenta M, cyan C and black K, respectively, and the four developing units 30 supply developers of Y, M, C and K to the photosensitive belt 14, respectively.

The developing unit 30 includes a developer supply unit 32 supplying a developer, and a developing bath 31 collecting developer dropped from the photosensitive belt 14 and resupplying the collected developer to the developer supply unit 32. The developing bath 31 includes a developing roller 36, a brush roller 37 for removing developer from the developing roller 36, a squeeze roller 34 for separating a liquid carrier regardless of image forming, from the developer supplied to the photosensitive belt 14 and a plate 35 for collecting the carrier flowing through the squeeze roller 34 to the developing bath 31.

The developer stored in the developing bath 31, the liquid carrier (norpor; N) of the solvent in the developer supply portion 38, and a toner of a developing material or a developer of high concentration in the developer supply portion 38 can be supplied to the developing supply unit 32. The developer stored in the developer supply unit 32 is supplied between the developing roller 36 and the photosensitive belt 14 by driving a pump.

During printing of a liquid type printer, the light scanning unit 16 scans light beams on the photosensitive belt 14 circulating past the reset apparatus 15. An electrostatic latent image is formed on the photosensitive belt 14 by the scanned light, and the electrostatic latent image is developed by the developer supplied from the developer supply unit 32. A color image is formed on the photosensitive belt 14 by the light scanning units 16 scanning light beams of different color information, and the developing units 30 developing an image by a developer of a corresponding color. Most of the liquid carrier of the developer supplied to the photosensitive belt 14 from the developing units 30 during the development, regardless of the image formation, is returned into the developing bath 31. The color image formed on the photosensitive belt 14 by a toner of the developing material is first transferred to the transfer roller 21, having a portion thereof engaged to the photosensitive belt 14, via the drier 18 for removing liquid carrier remaining on the photosensitive belt 14, by movement of the photosensitive belt 14. The image on the transfer roller 21 is then transferred to a sheet of paper 23 by rotation of the transfer roller 21 and a fixing roller 22 where the sheet 23 is inserted and moved forward.

Meanwhile, in the above-described printing operation, when toner attached to the photosensitive belt 14 during the development partially remains on the photosensitive belt 14 without being transferred to the sheet 23, the toner may drop into the developing bath 31 of the developing unit 30 during circulation of the photosensitive belt 14. Particularly, if black toner contaminates the developing bath 31 having yellow developer through the photosensitive belt 14, the appropriate color cannot be produced. Thus, contamination of developer caused by a developing material of one color mixing with the developing bath 31 of another color must be checked, and when the contamination exceeds an allowable range, the developer must be appropriately replaced.

SUMMARY OF THE INVENTION

It is an objective of the present invention to provide an apparatus and method for measuring developer contamination of a printer capable of measuring the degree of contamination of a developer recovered into a developing bath due to mixture of developing materials of other colors.

To achieve the above objective, a developer contamination measuring apparatus of a printer comprises: a developer extracting pipe unit extracting a developer to measure the degree of contamination according to mixing of a developing material of other colors with respect to the developer in a developing unit supplying a developer to a photosensitive medium for partially recovering the supplied developer, including a first pipe portion having a first gap and a second pipe portion having a second gap; a light emitting unit radiating light to the first pipe portion and the second pipe portion; a light detecting unit detecting light reflected or transmitted from the first pipe portion and the second pipe portion to output first and second light receiving signals, respectively; and a developer contamination measuring unit controlling the light emitting unit, and calculating the degree of contamination due to mixing of other developing materials with the developer from the first and the second light receiving signals.

Also, to achieve the above object, a method for measuring developer contamination of a printer including a developer extracting pipe unit for extracting a test developer, with a first pipe portion having a first gap, and a second pipe portion having a second gap; a light emitting unit radiating light to the first and the second pipe portions; a light detecting unit detecting light reflected or transmitted from the first and the second pipe portions to output first and second light receiving signals, respectively; and a developer contamination measuring unit controlling the light emitting unit, and calculating the degree of contamination due to mixing of other developing materials into the developer from the first and the second light receiving signals output from the light detecting unit, comprises the steps of: obtaining a difference between the first light receiving signal and the second light receiving signal; and finding the degree of contamination corresponding to the difference with reference to a table in which the degree of contamination corresponding to the difference between the first light receiving signal and the second light receiving signal are recorded to calculate the degree of contamination with respect to the mixing of other developing materials with the developer.

BRIEF DESCRIPTION OF THE DRAWINGS

The above objectives and advantages of the present invention will become more apparent by describing in detail a preferred embodiment thereof with reference to the attached drawings in which.

DESCRIPTION OF THE PREFERRED EMBODIMENTS

Figure 2:
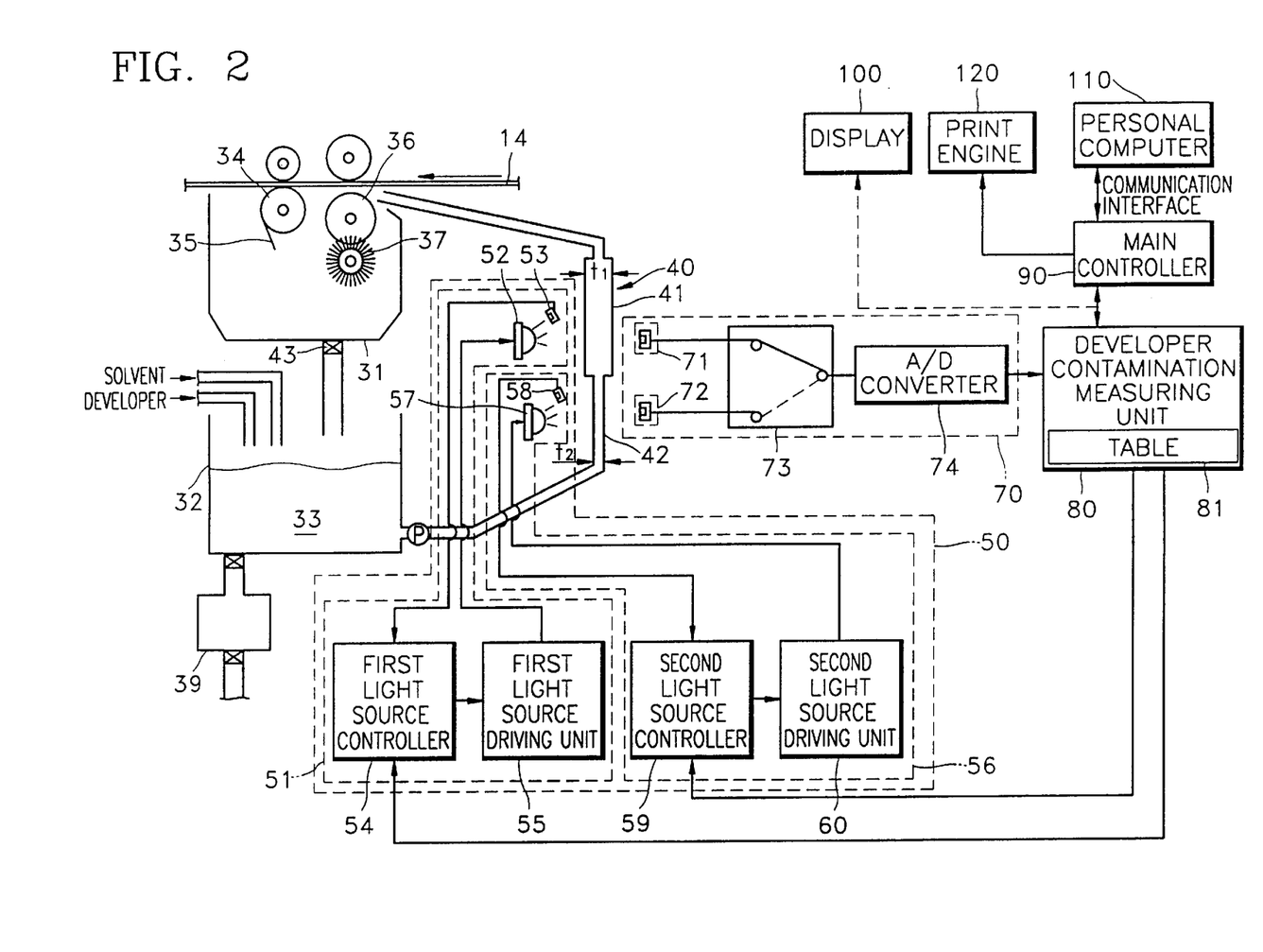
FIG. 2 shows a developer contamination measuring unit of a printer according to an embodiment of the present invention.

In FIG. 2, elements having the same function as those of FIG. 1 are represented by like reference numerals.

Referring to FIG. 2, an apparatus for measuring the contamination of a developer includes a developer extracting pipe unit 40, a light emitting unit 50, a light detecting unit 70 and a developer contamination measuring unit 80.

The developer extracting pipe unit 40 is provided on a developer supply pipe in which a developer supply unit 32 having a developer to be supplied to a photosensitive belt 14 is connected to a developing bath 31, and has a first pipe portion 41 and a second pipe portion 42 which are extended by gaps t1 and t2, respectively. Reference numeral 43 denotes a valve. The first gap t1 of the first pipe portion 41 and the second gap t2 of the second pipe portion 42 are determined such that the precision in measuring the contamination of an objective developer 33 is increased. The developer extracting pipe unit 40 may be provided in the developing bath 31 or the developer supply unit 32.

The light detecting unit 70 includes a first light detector 71 detecting light transmitted through the first pipe portion 41 to output a signal corresponding to the received light, a second light detector 72 detecting light transmitted through the second pipe portion 42 to output a signal corresponding to the received light, a switching portion 73 selectively outputting a signal input from the first light detector 71 and the second light detector 72 in accordance with a selection signal of a developer contamination measuring unit 80, and an analog-to-digital converter 74 converting an analog signal output from the switching portion 73 into a digital signal to output the converted signal.

The light emitting unit 50 includes a first light emitter 51 radiating light to the first pipe portion 41, and a second light emitter 56 radiating light to the second pipe portion 42.

The first light emitter 51 includes a first light source 52 radiating light to the first pipe portion 41, a third light detector 53 detecting part of the light emitted from the first light source 52 to constantly power the light emitted from the first light source 52, a first light source controller 54 controlling the amount of light emitted from the first light source 52 in accordance with an output signal corresponding to the light received from the third light detector 53 and a first light source driving portion 55 controlled by the first light source controller 54 to drive the first light source 52.

The second light emitter 56 includes a second light source 57 radiating light to the second pipe portion 42, a fourth light detector 58 detecting part of the light emitted from the second light source 57 to constantly power the light emitted from the second light source 57, a second light source controller 59 controlling the amount of light emitted from the second light source 57 in accordance with a signal output corresponding to the light received from the fourth light detector 58 and a second light source driving portion 60 controlled by the second light source controller 59 to drive the second light source 57.

The developer contamination measuring unit 80 controls the first light source controller 54 and the second light controller 59, outputs a selection signal to the switching portion 73, and calculates the amount of contamination of the developer 33 using first and second light receiving signals corresponding to the received light of the first and the second light detectors 71 and 72 through the analog-to-digital converter 74.

The concentration and amount of contamination in the developer 33 stored in the developer supply unit 32 are changed by mixing ratio of a solvent and/or a developer supplied from the developer supply portion (see 38 of FIG. 1) and the developer supplied from the developer bath 31. Thus, when a predetermined amount of light is radiated to the developer in the developer extracting pipe unit 40, the amount of light transmitted through the developer is changed in accordance with the concentration and the amount of contamination of the developer. The concentration and amount of the contamination of the developer are changed by consumption of the supplied toner and evaporation of the liquid carrier even when no developer is supplied by portion 38 (see FIG. 1). Thus, the amount of contamination due to mixing of another developing material cannot be precisely measured by light receiving information obtained by irradiating light to the pipe where the developer is filled, and detecting the amount of light transmitted through or reflected from the radiated pipe.

Figure 3:
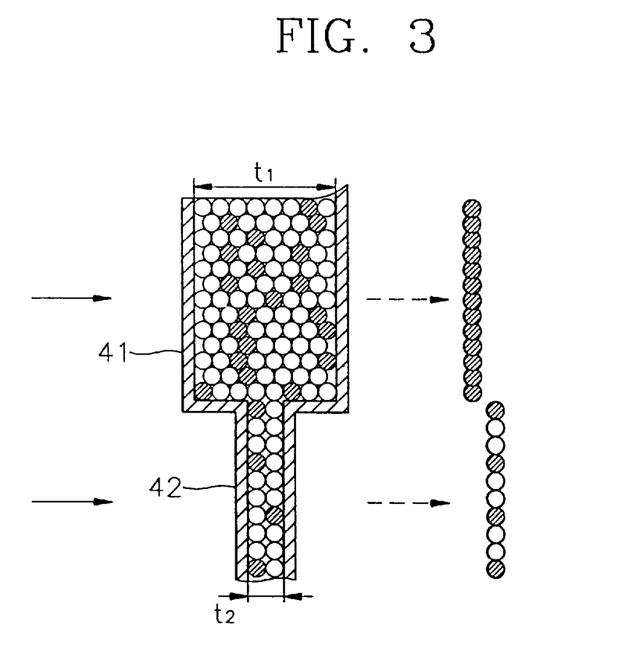
FIG. 3 is a schematic view showing the principle of generating a difference in the amounts of transmitted light in accordance with the difference in gaps of the developer extracting unit of FIG. 2 with respect to the same developer.

Thus, according to the present invention, first and second light receiving signals obtained from the developer stored in the first pipe portion 41 and the second pipe portion 42, the internal gaps of which are different from each other to accurately calculate the amount of contamination are used. For instance, referring to FIG. 3 showing the case in which 20% of a developer of another color is mixed with the developer, in an area of the developer (hatched portion) of the other color projected to a cross section vertical to the optical transmission proceeding direction when light is irradiated in the direction of the arrow, the first pipe portion 41 having a relatively wider gap t1 has the other developer of a contamination material occupying all of the cross-section, while the second pipe portion 42 having a relatively narrower gap t2 has the other developer of a contamination material occupying part of the cross section. When an equal amount of light is irradiated to the first pipe portion 41 and the second pipe portion 42 with respect to the developer contaminated by the above characteristic, the amounts of transmitted light are different, so that the first and the second output light receiving signals are different. Thus, a change in the amount of transmitted light due to a change in the concentration of the pure toner or a change in the transmitted light due to mixing of other developing material can be estimated from the first light receiving signal value. At this time, when the concentration of pure toner capable of estimating from the first light receiving signal matches the concentration of the pure toner capable of estimating from the second light receiving signal, it can be understood that the concentration of the pure toner of the developer has changed.

However, when the concentration of pure toner capable estimated from the first light receiving signal is different from that of the pure toner estimated from the second light receiving signal, it can be understood that the amount of light transmitted due to mixing of the contamination material is changed. From the above principle, the developer contamination measuring unit 80 includes a table in which concentrations of a pure toner and the degree of concentration corresponding to values of the first and second light receiving signals are recorded, and calculates the degree of contamination with reference to the table.

To easily calculate the degree of contamination, preferably, the first gap t1 and the second gap t2 are appropriately selected such that the difference between the first and the second light receiving signals is a single value with respect to a change in concentration of the pure toner and a change due to contamination within the predetermined measurement range. Then, the contamination value and the concentration value of the pure developer corresponding to a difference between the first light receiving signal and the second light receiving signal are empirically obtained and the obtained values are recorded in a table 81 of a memory of the developer contamination measuring unit 80, and the developer contamination measuring unit 80 obtains a difference value between the received first light receiving signal and the received second light receiving signal, and calculates the contamination value corresponding to the difference with reference table of the light receiving difference and contamination value.

Hereinafter, a process of calculating the difference between the first light receiving signal and the second light receiving signal, and the contamination value from the difference will be described.

First and second gaps t1 and t2 having a single value within the predetermined contamination measurement range in which a difference between the first light receiving signal and the second light receiving signal is predetermined with respect to a change in concentration of the pure toner and a change due to contamination are calculated by experiments.

Figure 4A:
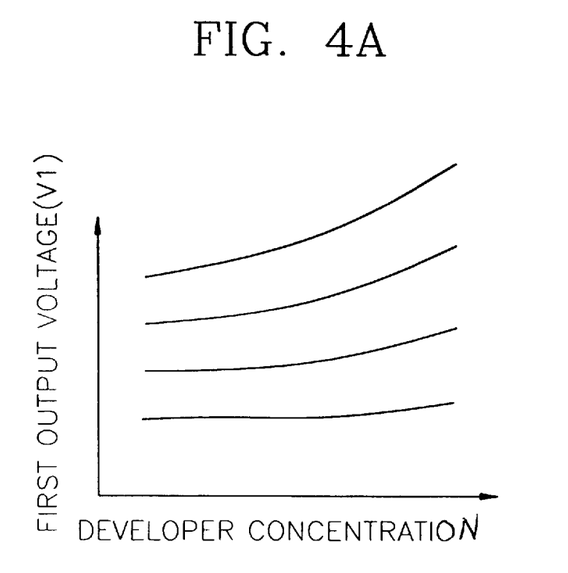
FIG. 4A is a graph of an example of an output voltage of a light detector corresponding to the transmitted light of a first pipe portion according to the concentration of a pure developer with respect to a difference in contamination of the developer.
Figure 4B:
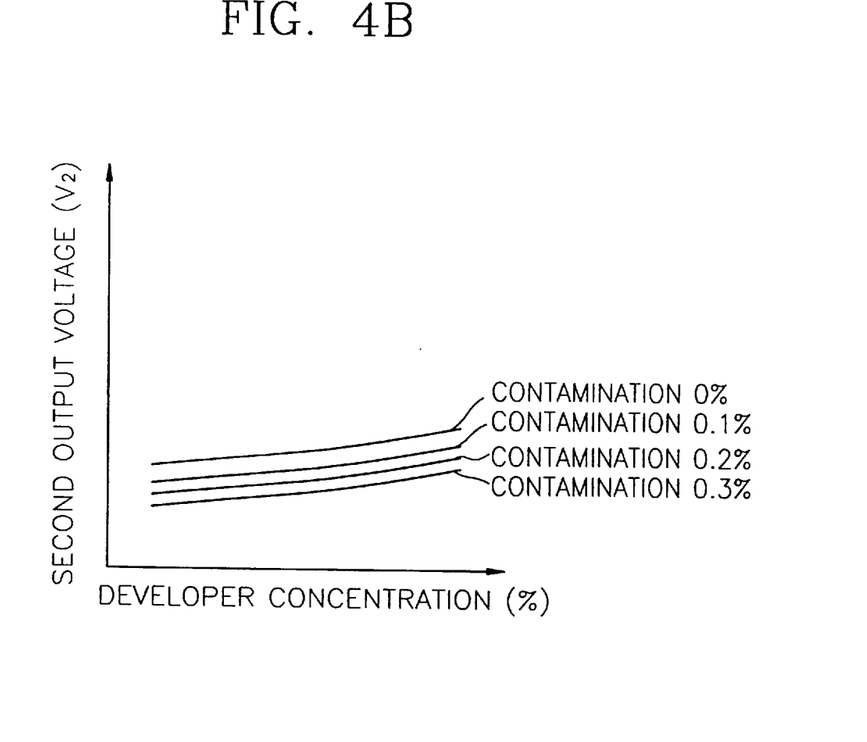
FIG. 4B is a graph of an example of an output voltage of a light detector corresponding to the transmitted light of a second pipe portion according to the same concentration as that of FIG. 4A.
Figure 4C:
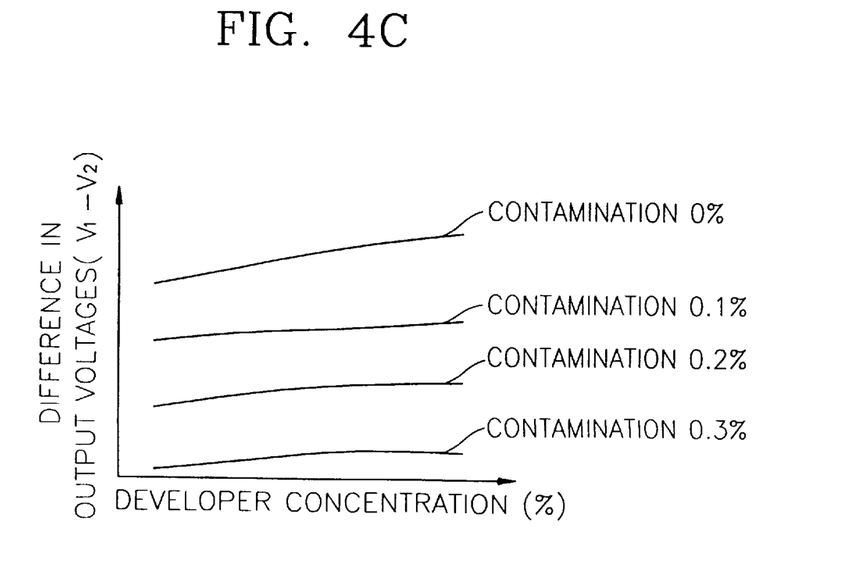
FIG. 4C is a graph of a difference in output voltages with respect to the concentration of the developer of FIGS. 4A and 4B according to the difference in contamination of the developer.

For instance, in arbitrarily selected first and second gaps t1 and t2, the amount of received light of the first pipe portion 41 and the second pipe portion 42 in accordance with contamination of other developing materials with respect to a change in concentration of a pure toner, i.e., a first output voltage v1 and a second output voltage v2 are obtained, with contamination intervals of 0.1%, as shown in FIGS. 4A and 4B, and a difference value between the output voltages V1 and V2, i.e., (V1−V2) is shown in FIG. 4C. Referring to FIG. 4C, the concentration and the amount of contamination corresponding to the difference in output voltages V1 and V2 have a single value. Thus, when the result with respect to the arbitrarily selected gaps t1 and t2 is obtained as shown in FIG. 4C, the gaps t1 and t2 are adopted to the first pipe portion 41 and the second pipe portion 42.

When the gaps t1 and t2 are determined, information as shown in FIG. 4C, i.e., data with respect to the concentration and the amount of contamination of the pure developer corresponding to the difference (V1−V2) in output voltages corresponding to a difference between the first light receiving signal and the second light receiving signal is recorded in the table 81 in the developer contamination measuring unit 80.

After the above described process is completed, the developer contamination can be measured. That is, the developer contamination measuring unit 80 obtains the difference between the first light receiving signal and the second light receiving signal, and calculates the contamination corresponding to the difference using the table 81.

Figure 5A:
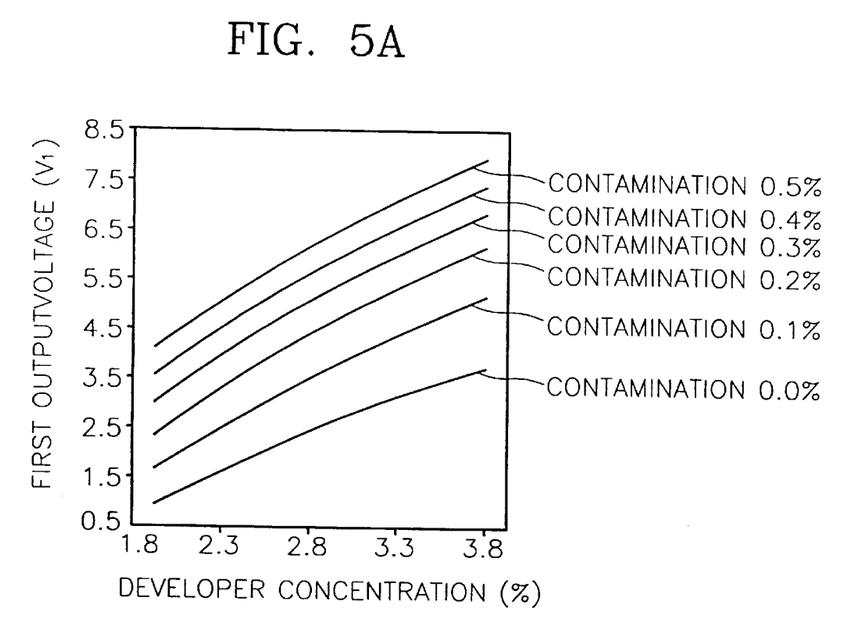
FIG. 5A is a graph of an output voltage corresponding to the transmitted light of the first pipe portion having a gap of 6 mm with respect to the concentration of a yellow developer according to the difference in contamination of the developer.
Figure 5B:
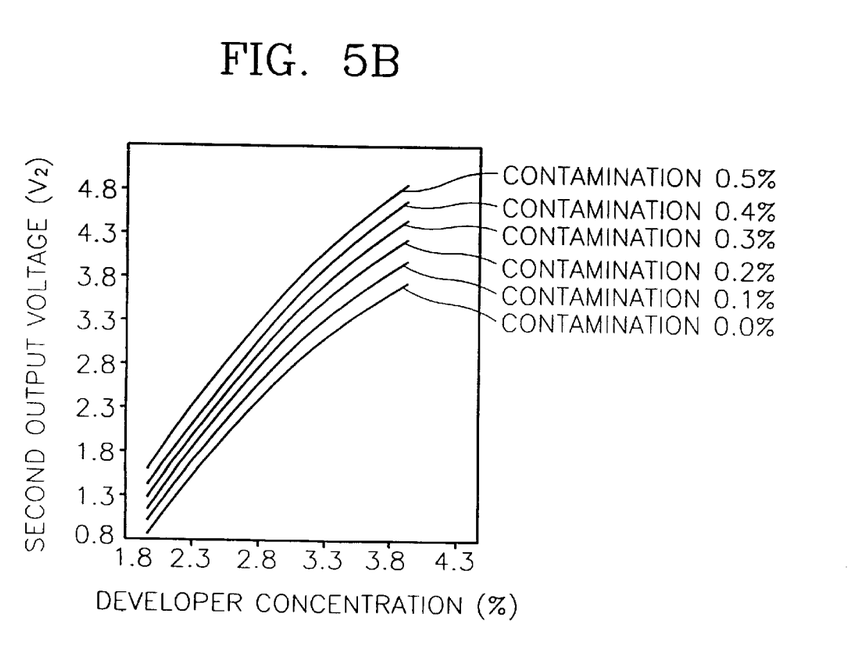
FIG. 5B is a graph of an output voltage corresponding to the transmitted light of the second pipe having a gap of 1 mm with respect to the concentration of a yellow developer according to the difference in contamination of the developer.
Figure 6:
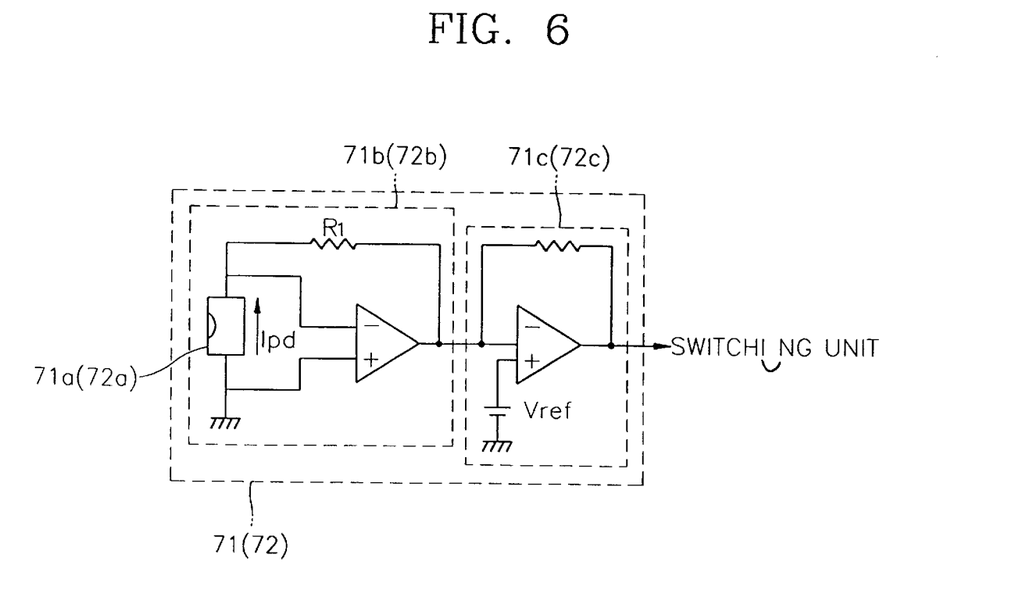
FIG. 6 is a circuit diagram of an internal circuit of a light detecting unit for generating an output voltage corresponding to the transmitted light of FIGS. 5A and 5B.

FIGS. 5A and 5B show first and second output voltages V1 and V2 corresponding to the light transmitted through the first pipe portion 41 and the second pipe portion 42 in the case in which a developer containing a yellow pure toner used for a liquid printer is mixed with contaminants of a black toner of 0%, 0.1%, 0.2%, 0.3%, 0.4% and 0.5% . The first gap t1 of the first pipe portion 41 is 6 mm, and the second gap t2 is 1 mm. Here, as shown in FIG. 6, internal circuits of the light detectors 71 and 72 further include inversion circuits 71*c* and 72*c* as well as light receiving units 71*b* and 72*b* outputting a voltage signal proportional to an output current $I_{pd}$ corresponding to the amount of received light of the light receiving members 71*a* and 72*a*. Thus, voltage signals obtained by inverting an output voltage Ipd×R1 corresponding to the received light of the light receiving units 71*b* and 72*b* through inversion circuits 71*c* and 72*c* are output to the switching unit 73 as first and second light receiving signals. A reference voltage Vref of the inversion circuits 71*c* and 72*c* is appropriately determined with respect to the sensitivity of each of the light receiving units 71*b* and 72*b* such that a deviation of the light receiving sensitivities between the light receiving units 71*b* and 72*b* is reduced. Output voltages of the inversion circuits 71*c* and 72*c* are shown as output voltages of FIGS. 5A and 5B. The inversion circuits 71*c* and 72*c* are for increasing the output voltages in accordance with an increase in the amount of contamination. However, when the output signals of the light receiving units 71*b* and 72*b* are output as the first and the second light receiving signals without employing the inversion circuits 71*c* and 72*c*, the output voltage is lowered according to the increase in the contamination, which are shown in FIGS. 4A and 4B.

Figure 5C:
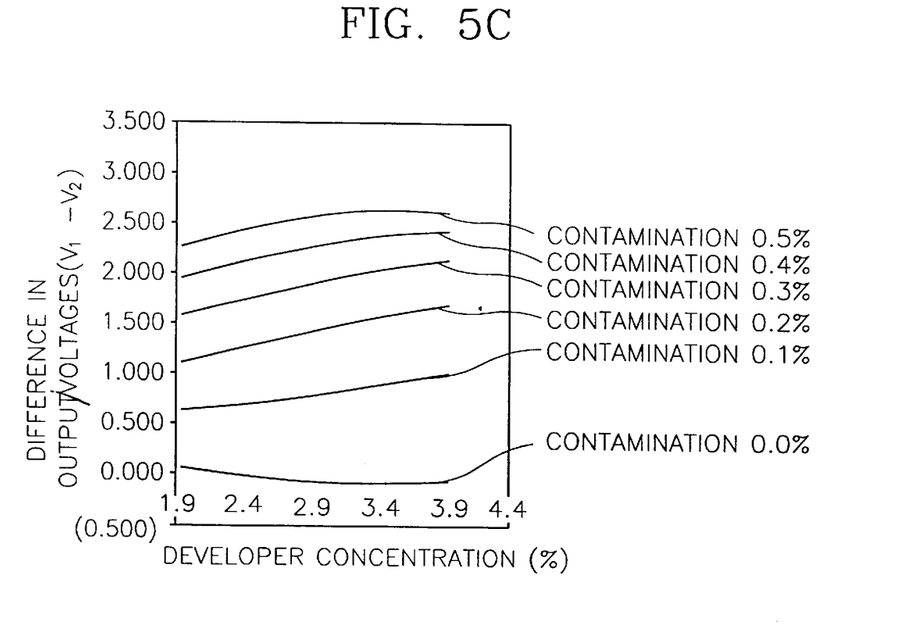
FIG. 5C is a graph of the difference in the output voltages of FIGS. 5A and 5B with respect to the concentration of a yellow developer according to different levels of contamination of the developer.

The contamination values corresponding to the difference (V1–V2) of the output voltages corresponding to the light receiving signals obtained by employing a circuit of FIG. 6 is shown in FIG. 5C.

When the concentration range of the pure developer satisfying the printing conditions is 2.4 to 3.4%, and a predetermined allowable contamination value is 0.5%, the contamination value corresponding to the difference between the light receiving signals has a single value within an error range of 0.1% and the above condition. Also, when the concentration of the pure developer in the developing bath 31 is within 2.4~3.4%, the resultant information of FIG. 5C and the gaps t1 and t2 adapted to the information can be adapted to the apparatus for measuring developer contamination.

Meanwhile, when the concentration range and the predetermined allowable contamination range of the pure developer are higher than the above-described range, the gaps of the first and the second pipe portions 41 and 42 having a signal difference between the light receiving signals with respect to the amount of contamination and the concentration of the pure toner must be obtained by experiments.

Also, the gaps t1 and t2 of the first pipe portion 41 and the second pipe portion 42 can be adapted to any case in which the difference between the first and the second light receiving signals has a single value with respect to the amount of contamination and concentration of the pure developer within the allowable range of the concentration of the pure developer and the predetermined contamination satisfying the printing conditions.

When the amount of contamination of the developer is calculated by the above method, the developer contamination measuring unit 80 outputs information of the calculated contamination to a display 100 outside the printer body. When the display 100 is directly connected to the developer contamination measuring apparatus (denoted by dotted lines), the contamination information is directly output to the display 100, and when the display 100 is controlled by a main controller 90 controlling the entire printer, the contamination information is transferred to the display 100 through the main controller 90. It is also preferable that the contamination information is transferred to a personal computer 110 connected through a communication interface through the main controller 90. When the contamination with respect to the developer is outside the allowable range, the developer contamination measuring unit 80 transfers a message requiring replacement of the developer to the display 100 and/or the computer 110.

When contamination of the developer exceeds the allowable contamination value, the developer contamination measuring unit 80 drains the developer 33 in the developer supply unit 32 to the waste tank 39 for collecting waste developer. Then, new developer to be used for printing is supplied into the developer supply unit 32 from the developer supply portion 38 (see FIG. 1).

The main controller 90 receives print data from the computer 110 and processes the received printing data as an image data corresponding to a print engine 120 to output the processed image data to the print engine 120. The print engine 120 includes a reset apparatus, a developing unit, a light scanning unit, a drier, a transfer apparatus and a paper supply unit (not shown) (see FIG. 1).

Figure 7:
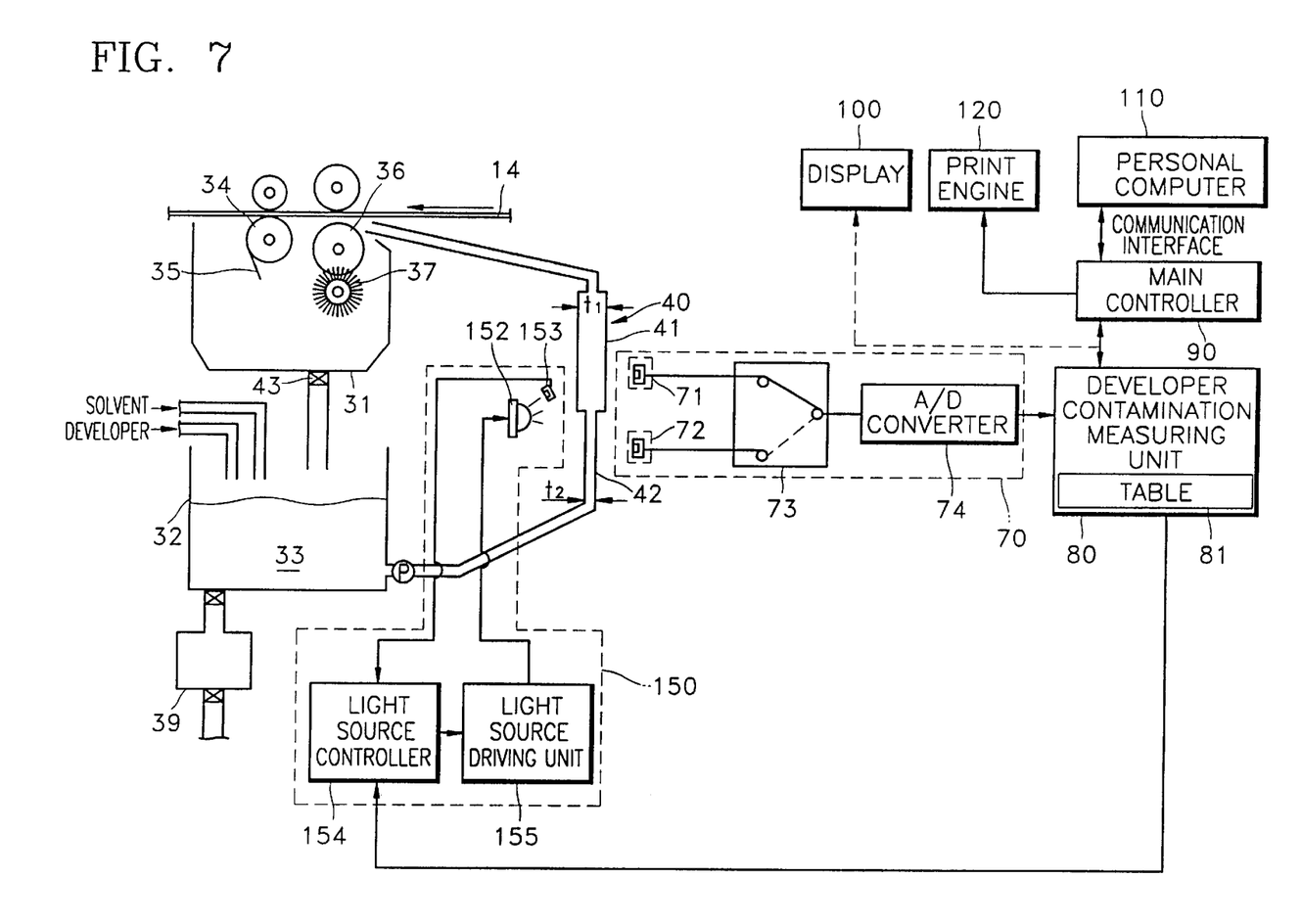
FIG. 7 is a diagram of an apparatus for measuring contamination of a developer of a printer according to another embodiment of the present invention.

Elements in FIG. 7 that are the same elements as those of FIG. 2 are denoted by like reference numerals.

Referring to FIG. 7, the developer contamination measuring apparatus includes a light emitting unit 150, a light detecting unit 70 and a developer contamination measuring unit 80.

The light emitting unit 150 includes a light source 152, a light detector 153, a light source controller 154 and a light source driving unit 155.

A central axis of the output light of one light source 152 is arranged facing a boundary region between the first pipe portion 41 and the second pipe portion 42 such that light is irradiated on the first pipe portion 41 and the second pipe portion 42, which is different from the developer contamination measuring apparatus of FIG. 2.

The light detector 153 partially detects light output from the light source 152 to output a signal corresponding to the received light. The light source controller 154 controls the amount of light emitted from the light source 152 according to the signal output of the light detector 153 corresponding to the received light, and the light source driving unit 155 is controlled by the light source controller 154 to drive the light source 152.

The developer contamination measuring unit 80 controls the light source controller 154.

The developer contamination measuring apparatus can reduce the number of elements of the light emitting unit 150.

As described above, according to the developer contamination measuring apparatus and a method of measuring the developer contamination, the contamination due to mixing of other developing materials in the pure developer can be precisely measured, and when the calculated amount of contamination is outside the allowable contamination value range, the developer can be appropriately replaced to thereby suppress deterioration of print quality.

What is claimed is:

1. A developer contamination measuring apparatus of a printer comprising:

a developer extracting pipe unit which extracts a developer to measure a degree of contamination due to mixing of another developing material with the developer in a developing unit supplying the developer to a photosensitive medium for partially recovering the supplied developer, including a first pipe portion having a first gap and a second pipe portion having a second gap;

a light emitting unit radiating light to the first pipe portion and the second pipe portion;

a light detecting unit detecting light reflected or transmitted from the first pipe portion and light reflected or transmitted from the second pipe portion to output first and second light receiving signals, respectively; and a developer contamination measuring unit controlling the light emitting unit, and calculating the degree of contamination due to mixing of another developing material with the developer based on the first and the second light receiving signals.

2. The developer contamination measuring apparatus of claim 1, wherein the developer contamination measuring unit includes a table in which the degree of contamination corresponding to a difference between the first light receiving signal and the second light receiving signal is recorded to calculate the contamination from the difference between the first light receiving signal and the second light receiving signal.

3. The developer contamination measuring apparatus of claim 1, wherein the light detecting unit comprises:

a first light detector detecting the light reflected or transmitted from the first pipe portion;

a second light detector detecting the light reflected or transmitted from the second pipe portion; and an analog-to-digital converter converting a signal output from the first light detector and the second light detector to a digital signal to output the converted signal to the developer contamination measuring unit.

4. The developer contamination measuring apparatus of claim 3, further comprising a switching unit selectively outputting one of input signals corresponding to received light from the first light detector and the second light detector in accordance with a selected signal from the developer contamination measuring unit.

5. The developer contamination measuring apparatus of claim 1, wherein the light emitting unit comprises:
   a first light emitting unit radiating light to the first pipe portion; and
   a second light emitting portion radiating light to the second pipe portion.

6. The developer contamination measuring apparatus of claim 5, wherein the first light emitting unit comprises:
   a first light source radiating light to the first pipe portion;
   a third light detector partially detecting light output from the first light source and outputting a corresponding light output signal;
   a first light source controller constantly controlling the amount of emitted light of the first light source from the light output signal; and
   a first light source driver controlled by the first light source controller to drive the first light source.

7. The developer contamination measuring apparatus of claim 5, wherein the second light emitting unit comprises:
   a second light source radiating light to the second pipe portion;
   a fourth light detector partially detecting light emitted from the second light source and outputting a corresponding light output signal;
   a second light source controller constantly controlling the amount of emitted light by the second light source from the light output signal; and
   a second light source driver controlled by the second light source controller to drive the second light source.

8. The developer contamination measuring apparatus of claim 1, wherein information on the contamination calculated from the developer contamination measuring unit is indicated through a display.

9. The developer contamination measuring apparatus of claim 8, wherein the developer contamination measuring unit transmits a message to the display informing a user to replace the developer when the calculated degree of contamination of the developer exceeds a predetermined allowable degree of contamination.

10. The developer contamination measuring apparatus of claim 1, wherein the developer contamination measuring unit drains the developer in the developing unit to a waste tank for collecting the waste developer, when the measured amount of contamination of the developer exceeds a predetermined allowable degree of contamination.

11. The developer contamination measuring apparatus of claim 10, wherein the developer contamination measuring unit supplies a new developer of the developer supply portion to the developing unit after the developer in the developing unit is drained to the waste tank.

12. The developer contamination measuring apparatus of claim 1, wherein the developer contamination measuring unit supplies information on the calculated amount of contamination to a computer connected through a communication interface.

13. The developer contamination measuring apparatus of claim 12, wherein the developer contamination measuring unit transmits a message informing a user to replace the developer, when the calculated degree of contamination of the developer exceeds a s predetermined allowable degree of contamination.

14. A method for measuring developer contamination of a printer including a developer extracting pipe unit for extracting a test developer, with a first pipe portion having a first gap, and a second pipe portion having a second gap; a light emitting unit radiating light to the first and the second pipe portions; a light detecting unit detecting light reflected or transmitted from the first and the second pipe portions to output first and second light receiving signals, respectively; and a developer contamination measuring unit controlling the light emitting unit, and calculating the degree of contamination due to mixing of other developing materials into the developer from the first and the second light receiving signals output from the light detecting unit, comprising the steps of:
   (a) obtaining a difference between the first light receiving signal and the second light receiving signal; and
   (b) finding the degree of contamination corresponding to the difference with reference to a table in which the degree of contamination corresponding to the difference between the first light receiving signal and the second light receiving signal are recorded to calculate the degree of contamination with respect to the mixing of other developing materials with the developer.

* * * * *